United States Patent [19]
Carpenter

[11] Patent Number: 6,103,530
[45] Date of Patent: Aug. 15, 2000

[54] CULTURES OF HUMAN CNS NEURAL STEM CELLS

[75] Inventor: Melissa Carpenter, Lincoln, R.I.

[73] Assignee: Cytotherapeutics, Inc., Lincoln, R.I.

[21] Appl. No.: 09/178,035

[22] Filed: Oct. 23, 1998

Related U.S. Application Data

[62] Division of application No. 08/926,313, Sep. 5, 1997.

[51] Int. Cl.$^7$ ...................................................... C12N 5/00
[52] U.S. Cl. .......................... 435/405; 435/325; 435/368; 435/377; 435/384; 435/387; 435/389; 435/404; 435/406
[58] Field of Search ..................................... 435/325, 368, 435/377, 384, 387, 389, 404, 405, 406

[56] References Cited

U.S. PATENT DOCUMENTS

| | | | |
|---|---|---|---|
| 4,753,635 | 6/1988 | Sagen et al. ................................. | 60/49 |
| 4,980,174 | 12/1990 | Sagen et al. ............................ | 424/563 |
| 5,082,670 | 1/1992 | Gage ....................................... | 424/520 |
| 5,175,103 | 12/1992 | Lee et al. ................................ | 435/172.3 |
| 5,411,883 | 5/1995 | Boss et al. ............................. | 435/240.2 |
| 5,580,777 | 12/1996 | Bernard et al. ....................... | 435/240.2 |
| 5,612,211 | 3/1997 | Wilson et al. ........................... | 435/378 |
| 5,639,618 | 6/1997 | Gay ........................................ | 435/7.21 |
| 5,672,499 | 9/1997 | Anderson et al. .................... | 435/240.2 |
| 5,688,692 | 11/1997 | Jat .......................................... | 435/354 |
| 5,750,376 | 5/1998 | Weiss et al. .......................... | 435/69.52 |
| 5,753,506 | 5/1998 | Johe ....................................... | 435/377 |

FOREIGN PATENT DOCUMENTS

| | | |
|---|---|---|
| WO 89/03872 | 5/1989 | WIPO . |
| WO 90/06757 | 6/1990 | WIPO . |
| WO 91/02003 | 2/1991 | WIPO . |
| WO 91/09936 | 7/1991 | WIPO . |
| WO 91/17141 | 11/1991 | WIPO . |
| WO 93/01275 | 1/1993 | WIPO . |
| WO 93/09802 | 5/1993 | WIPO . |
| WO 94/09119 | 4/1994 | WIPO . |
| WO 94/10292 | 5/1994 | WIPO . |
| WO 94/16718 | 8/1994 | WIPO . |
| WO 95/00632 | 1/1995 | WIPO . |
| WO 96/15226 | 5/1996 | WIPO . |

OTHER PUBLICATIONS

Anchan et al., "EGF and TGF–. . Stimulate Retinal Neuroepithelial Cell Proliferation in Vitro," *Neuron*, 6(6):923–936 (1991).

Andres "Removal and reimplantation of the parietal cortex of mice during the first nine days of life: consequences for the barrelfield" *Journal of Neural Transplantation* 1(1):11–12 (1989) (abstract).

Blakemore & Crang., "Extensive Oligodendrocyte Remyelination Following Injection of Cultured Central Nervous System," *Developmental Neuroscience*, 10:1–11 (1988).

Bossart et al., "Epidermal growth factor stimulates colony formation and non–neuronal marker protein expression by human neuroblastoma in methylcellulose culture", *Anticancer Res.* 9: 1496–1504, (1989).

Calof et al., "Regulation of Neurogenesis and neuronal differentiation in primary and immortalized cells from Mouse olfactory epithellum", *J. Cell Biol.* 109(4 part 2): 57A, (1989).

Calof et al., "Analysis of Neurogenesis in a Mammalian Neuroepithelium: Proliferation and Differentiation of an Olfactory Neuron Precursor in Vitro," *Neuron*, 3:115–127 (1989).

Cattaneo and McKay., "Proliferation and differentiation of neuronal stem cells regulated by nerve growth factor," *Nature*, 347:762–765 (1990).

Cattaneo et al., "Non–virally mediated gene transfer into human central nervous system precursor cells", *Mol. Brain Res.*, 42: 161–66, (1996).

Cepko et al., "Immortalization of neural cells via retrovirus–mediated oncogene transduction," *Ann. Rev. Neurosci.*, 12:47–65 (1989).

Drago et al., "Fibroblast growth factor–mediated proliferation of central nervous system precursors depends on endogenous production of insulin–like growth factor I", *Proc. Natl. Acad. Sci. USA* 88(6): 2199–21203, (1991).

Federoff et al. "Expression of nerve growth factor in vivo from a defective herpes simplex virus 1 vector prevents effects of axotomy on sympathetic ganglia" (*Proc. Natl. Acad. Sci. USA* 89(5): 1636–1640, 1992).

Franklin et al., "Transplanted type–1 astrocyystes facilities repair of demyelinating lesions by host oligodendrycytes in adult rat spinal cord", *Neuropathol Appl Neurobiol* 17(3), 244, (1991).

Frederiksen et al., "Immortalization of precursor cells from the mammalian CNS," *Neuron*, 1:439–448 (1988).

Frederiksen et al., "Proliferation and differentiation of rat neuroepithelial precursor cells in vivo," *The Journal of Neuroscience* 8(4): 1144–1151 (1988).

Geller et al., "A Defective HSV–1 vector expresses *Escherichia coli* .β.–galactosidase in cultured peripheral neurons," *Science*, 241:1667–1669 (1988).

Gensburger et al., "Brain basic fibroblast growth factor stimulates the proliferation of rat neuronal precursor cells in vivo," *FEBS Letts*, 217(1):1–5 (1987).

Hall & Watt, "Stem cells: the generation and maintenance of cellular diversity," *Development*, 106:619–633 (1989).

Hammang et al., "Myelination following transplantation of EGF–responsive neural stem cells into a myelin–deficient environment", *Experimental Neurology* 147:84–95 (1997).

Hoffman et al., "Transplantation of a polymer–encapsulated cell line genetically engineered to release NGF," *Exp. Neurol.* 122:100–106 (1993).

(List continued on next page.)

*Primary Examiner*—Leon B. Lankford, Jr.
*Assistant Examiner*—Christopher R. Tate
*Attorney, Agent, or Firm*—Mintz, Levin, Cohn, Ferris, Glovsky and Popeo, P.C.; Ivor R. Elrifi; John T. Prince

[57] ABSTRACT

Isolation, characterization, proliferation, differentiation and transplantation of mammalian neural stem cells is disclosed.

2 Claims, 4 Drawing Sheets

OTHER PUBLICATIONS

Hunter et al., "Growth factor responses of enriched bipotential glial progenitors," *Developmental Brain Research,* 54(2):235–248 (1990).

Isacson et al., "A primate model of Huntingdon's disease: cross–species implantation of striatal precursor cells to the excitotoxically lesioned baboon caudate–putamen", *Exp. Brain, Res.* 75(1): 213–220, (1989).

Jaenisch et al., "The cells of primitive neuroectodermal tumours may undergo differentiation and, eventually, may be transformed to neurons, glial cells, and ependymal cells", *Acta Histochemica Supplementband* 42: 139–147, (1992).

Kaplan et al., "Neurogenesis in the 3–month–old rat visual cortex," *J. Comp. Neurol.,* 195:323 (1981).

Kesslak et al. (*Exp Neurology* 94(3): 615–626, 1989).

Kumar et al. "Identification of a Set of Genes with Developmental Down–Regulated Expression in the Mouse Brain," *Biochemical and Biophysical Research Comm.,* 185(3):1155–1161 (1992).

Lendahl et al., "CNS stem cells express a new class of intermediate filament protein," *Cell,* 60 585–595 (1990).

Lin et al., "GDNF: A Glial Cell Line–Derived Neurotrophic Factor Midbrain Dopaminergic Neuron," *Science,* 260:1130 (1993).

Lindvall et al. "Human fetal dopamine neurons grafted into the striatum in two patients with severe Parkinson's disease", (*Archives of Neurology* 46(6): 615–631, 1989).

Lo et al., "V–myc Immortalizationof Early Rat Neural Crest Cells Yields a Clonal Cell Line Which Generates Both Glial and Adrenergic Progenitor Cells," *Developmental Biology,* 145:139–153 (1991).

Morrison et al., "Trophic stimulation of cultured neurons from neonatal rat brain by epidermal growth factor," *Science,* 238:72–75 (1987).

Potten & Loeffler, "Stem cells: attributes, cycles, spirals, pitfalls and uncertainties. Lessons for and from the Crypt," *Development,* 110:1001–1020 (1990).

Price et al., "Cell lineage in the rat cerebral cortex: a study using retroviral–mediated gene transfer", *Development* 104(3): 473–482, (1988).

Raff et al., "A glial progenitor cell that develops in vitro into an astrocyte or an oligodendrocyte depending on culture medium," *Nature* 303:390–396 (1983).

Rakic, "Limits of neurogenesis in primates," *Science* 227:1054 (1985).

Reh et al., "Age of differentiation determines rat retinal germinal cell phenotype: Induction of differentiation by dissociation," *The Journal of Neuroscience,* 9(12):4179–4189 (1989).

Renfranz et al., "Region–specific differentiation of the hippocampal stem cell line HiB5 upon implantation into the developing mammalian brain" *Cell* 66:713–729 (1991).

Reynolds & Weiss., "Generation of neurons and astrocytes from isolated cells of the adult mammalian central nervous system," *Science,* 255:1707–1710 (1992).

Reynolds et al., "A multipotent EGF–responsive striatal embryonic progenitor cell produces neurons and astrocytes," *J. Neurosci.* 12(11):4565–4574 (1992).

Richardson et al., "A role for platelet–derived growth factor in normal gliogenesis in the central nervous system", *Cell,* 53: 309–319, 1988).

Snyder et al., "Multipotent neural cell lines can engraft and participate in development of mouse cerebellum", *Cell* 68:33–51 (1992).

Stemple & Anderson, "Isolation of a stem cell for neurons and glia from the mammalian neural crest", *Cell* 71:1–20, (1992).

Temple et al., "Divison and differentiation of isolated CNS blast cells in microculture," *Nature,* 340:471–473 (1989).

Tohyama et al., "Nestin expression in embryonic human neuroepithelium and in human neuroepithelial tumor cells", *Lab. Invest.,* 66: 303–313, (1992).

Vescovi et al., "Continual proliferation of EGF–dependent progenitor cells of the embryonic human CNS in vitro"*Society for Neuroscience Abstracts*, vol. 19, Abstract #360.12 (1993).

Wendt et al. "Regeneration of rat hippocampal fimbria fibers after fimbria transection and peripheral nerve or fetal hippocampal implantation.", (*Exp. Neurology* 79(2): 452–461, 1983).

Yamada et al., *Growth of cells in hormonally defined media*—Book A Cold Spring Harbor Laboratory, 1982— Cold Spring Harbor conferences on cell proliferation, vol. 9, 131–143.

CULTURES OF HUMAN CNS NEURAL STEM CELLS

RELATED APPLICATIONS

This is a divisional application of U.S. patent application Ser. No. 08/926,313, filed Sep. 5, 1997.

TECHNICAL FIELD OF THE INVENTION

This invention relates to isolation of human central nervous system stem cells, and methods and media for proliferating, differentiating and transplanting them.

BACKGROUND OF THE INVENTION

During development of the central nervous system ("CNS"), multipotent precursor cells, also known as neural stem cells, proliferate, giving rise to transiently dividing progenitor cells that eventually differentiate into the cell types that compose the adult brain. Neural stem cells are classically defined as having the ability to self-renew (i.e., form more stem cells), to proliferate, and to differentiate into multiple different phenotypic lineages, including neurons, astrocytes and oligodendrocytes.

These neural stem cells have been isolated from several mammalian species, including mice, rats, pigs and humans. See, e.g., WO 93/01275, WO 94/09119, WO 94/10292, WO 94/16718 and Cattaneo et al., *Mol. Brain Res.*, 42, pp. 161–66 (1996), all herein incorporated by reference.

Human CNS neural stem cells, like their rodent homologues, when maintained in a mitogen-containing (typically epidermal growth factor or epidermal growth factor plus basic fibroblast growth factor), serum-free culture medium, grow in suspension culture to form aggregates of cells known as "neurospheres". In the prior art, human neural stem cells have doubling rates of about 30 days. See, e.g., Cattaneo et al., *Mol. Brain Res.*, 42, pp. 161–66 (1996). Upon removal of the mitogen(s) and provision of a substrate, the stem cells differentiate into neurons, astrocytes and oligodendrocytes. In the prior art, the majority of cells in the differentiated cell population have been identified as astrocytes, with very few neurons (<10%) being observed.

There remains a need to increase the rate of proliferation of neural stem cell cultures. There also remains a need to increase the number of neurons in the differentiated cell population. There further remains a need to improve the viability of neural stem cell grafts upon implantation into a host.

SUMMARY OF THE INVENTION

This invention provides novel human central nervous system stem cells, and methods and media for proliferating, differentiating and transplanting them. In one embodiment, this invention provides novel human stem cells with a doubling rate of between 5–10 days, as well as defined growth media for prolonged proliferation of human neural stem cells. The invention also provides differentiated cell populations of human neural stem cells that provide previously unobtainable large numbers of neurons, as well as astrocytes and oligodendrocytes. This invention also provides novel methods for transplanting neural stem cells that improve the viability of the graft upon implantation in a host.

DETAILED DESCRIPTION OF THE INVENTION

Figure 1:
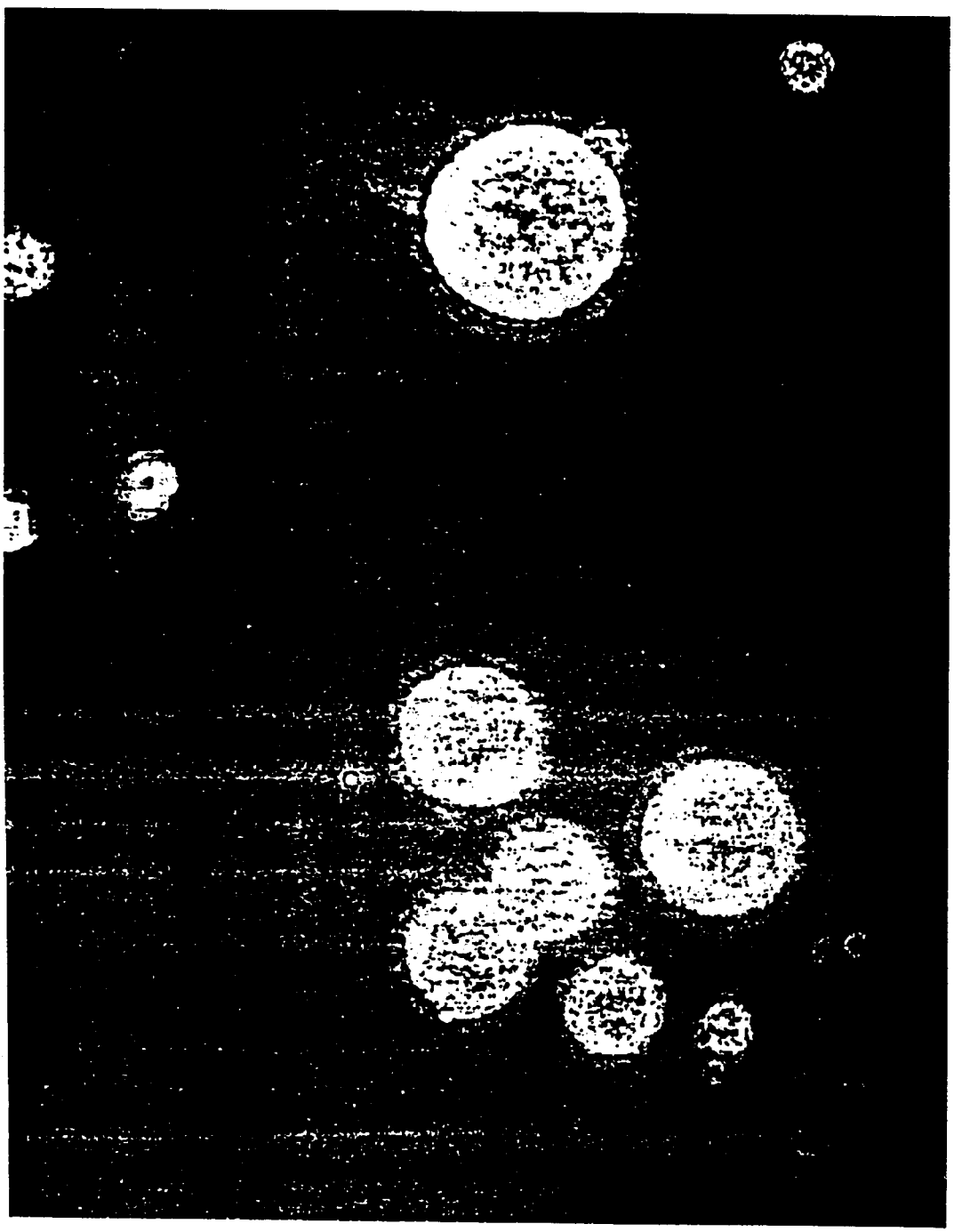
FIG. 1 shows a representation of spheres of proliferating 9 FBr human neural stem cells (passage 6) derived from human forebrain tissue.
Figure 2A:
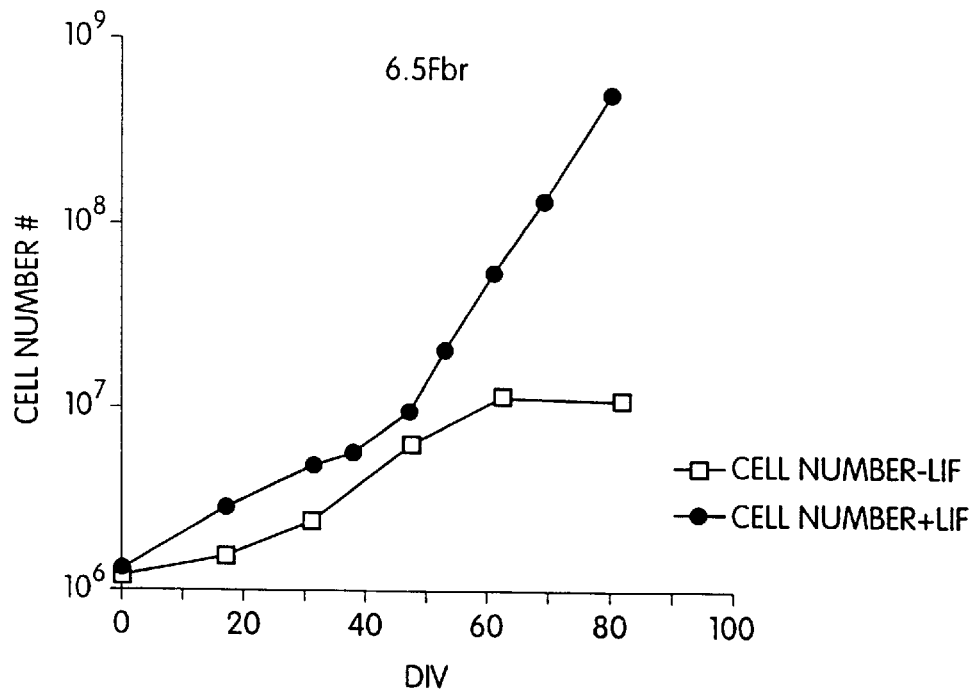
FIG. 2, Panel A, shows a growth curve for a human neural stem cell line designated 6.5 Fbr cultured in (a) defined media containing EGF, FGF and leukemia inhibitory factor ("LIF") (shown as closed diamonds), and (b) the same media but without LIF (shown as open diamonds); Panel B shows a growth curve for a human neural stem cell line designated 9 Fbr cultured in (a) defined media containing EGF, FGF and LIF (shown as closed diamonds), and (b) the same media but without LIF (shown as open diamonds); Panel C shows a growth curve for a human neural stem cell line designated 9.5 Fbr cultured in (a) defined media containing EGF, FGF and LIF (shown as closed diamonds), and (b) the same media but without LIF (shown as open diamonds); Panel D shows a growth curve for a human neural stem cell line designated 10.5 Fbr cultured in (a) defined media containing EGF, FGF and leukemia inhibitory factor ("LIF") (shown as closed diamonds), and (b) the same media but without LIF (shown as open diamonds).
Figure 2B:
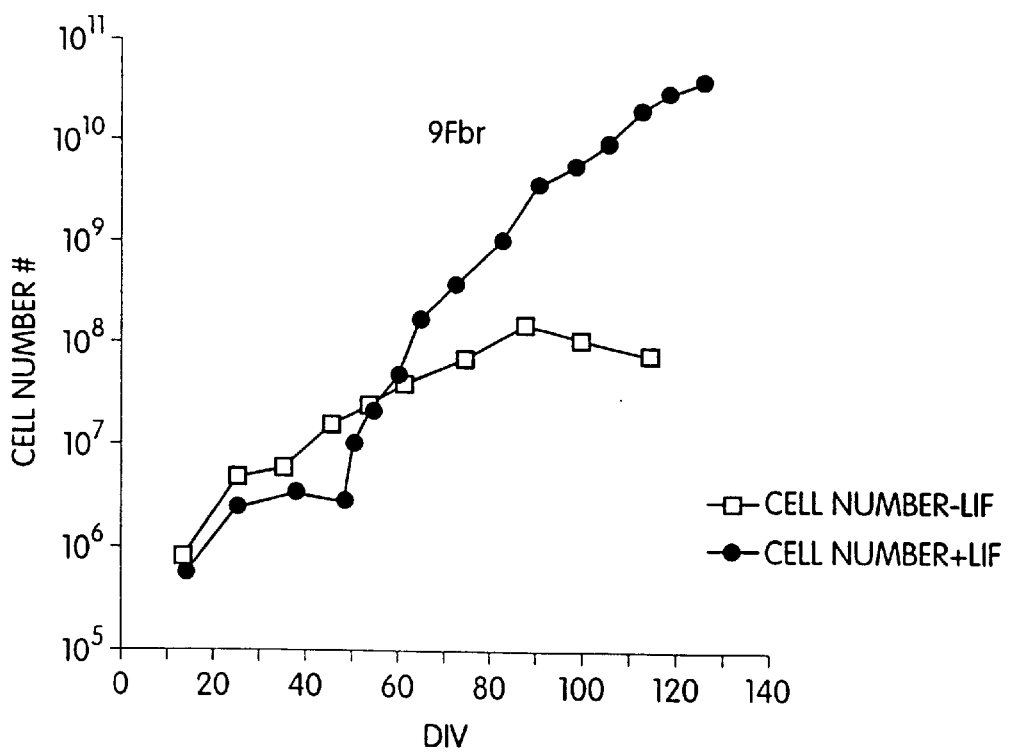
Figure 2C:
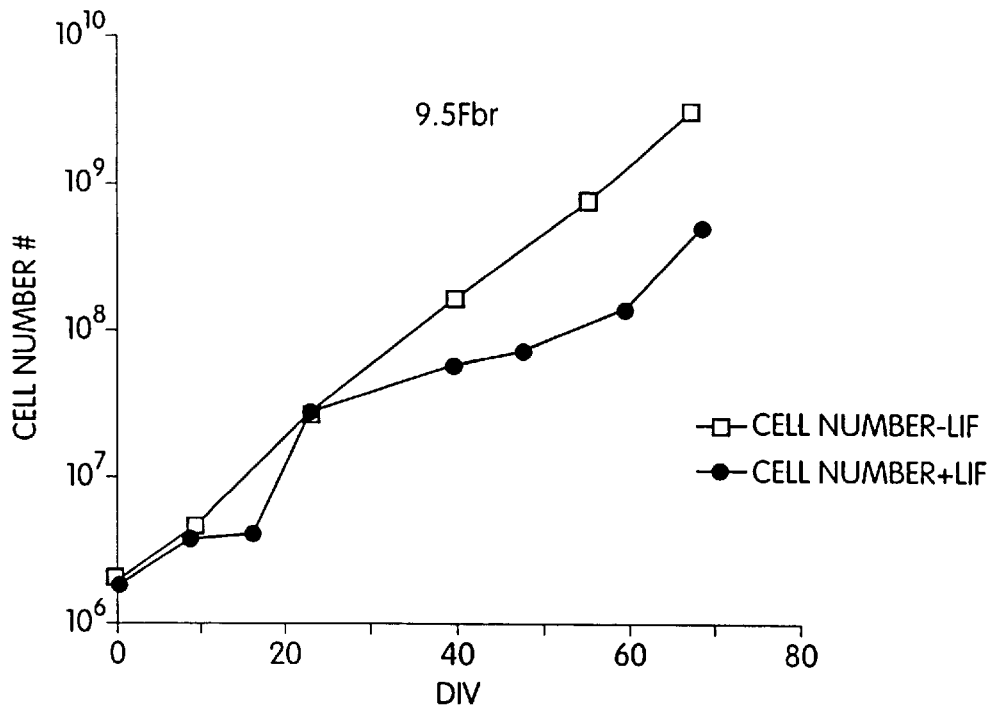
Figure 2D:
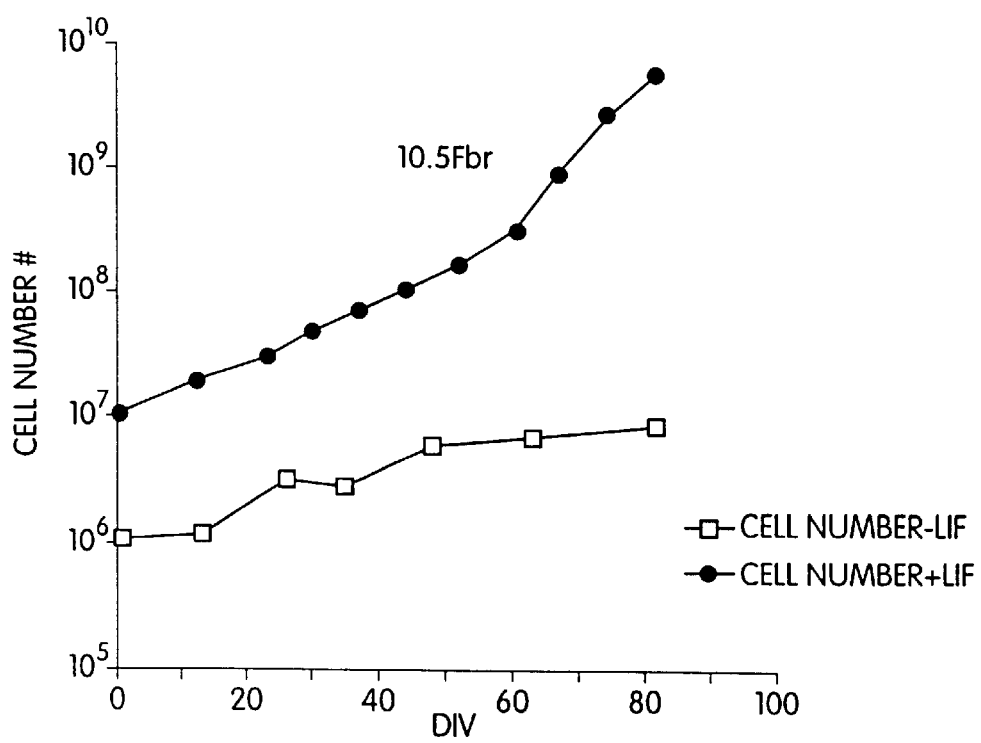

This invention relates to isolation, characterization, proliferation, differentiation and transplantation of CNS neural stem cells.

In one embodiment the invention provides novel human CNS stem cells isolated from the forebrain. We have isolated 4 neural stem cell lines from human forebrain, all of which exhibit neural stem cell properties; namely, the cells are self renewing, the cells proliferate for long periods in mitogen containing serum free medium, and the cells, when differentiated, comprise a cell population of neurons, astrocytes and oligodendrocytes. These cells are capable of doubling every 5–10 days, in contrast with the prior art diencephalon-derived human neural stem cells. Reported proliferation rates of diencephalon-derived human neural stem cells approximate one doubling every 30 days. See Cattaneo et al., *Mol. Brain Res.*, 42, pp. 161–66 (1996).

Any suitable tissue source may be used to derive the neural stem cells of this invention. Both allografts and autografts are contemplated for transplantation purposes.

This invention also provides a novel growth media for proliferation of neural stem cells. Provided herein is a serum-free or serum-depleted culture medium for the short term and long term proliferation of neural stem cells.

A number of serum-free or serum-depleted culture media have been developed due to the undesirable effects of serum which can lead to inconsistent culturing results. See, e.g., WO 95/00632 (incorporated herein by reference), and prior art medium described therein.

Prior to development of the novel media described herein, neural stem cells have been cultured in serum-free media containing epidermal growth factor ("EGF") or an analog of EGF, such as amphiregulin or transforming growth factor alpha ("TGF-a"), as the mitogen for proliferation. See, e.g., WO 93/01275, WO 94/16718, both incorporated herein by reference. Further, basic fibroblast growth factor ("bFGF") has been used, either alone, or in combination with EGF, to enhance long term neural stem cell survival.

The improved medium according to this invention, which contains leukemia inhibitory factor ("LIF"), markedly and unexpectedly increases the rate of proliferation of neural stem cells, particularly human neural stem cells.

We have compared growth rates of the forebrain-derived stem cells described herein in the presence and absence of LIF; unexpectedly we have found that LIF dramatically increases the rate of cellular proliferation in almost all cases.

The medium according to this invention comprises cell viability and cell proliferation effective amounts of the following components:

(a) a standard culture medium being serum-free (containing 0–0.49% serum) or serum-depleted (containing 0.5–5.0% serum), known as a "defined" culture medium, such as Iscove's modified DulbeccO's medium ("IMDM"), RPMI, DMEM, Fischer's, alpha medium, Leibovitz's, L-15, NCTC, F-10, F-12, MEM and McCoy's;

(b) a suitable carbohydrate source, such as glucose;

(c) a buffer such as MOPS, HEPES or Tris, preferably HEPES;

(d) a source of hormones including insulin, transferrin, progesterone, selenium, and putrescine;

(e) one or more growth factors that stimulate proliferation of neural stem cells, such as EGF, bFGF, PDGF, NGF, and analogs, derivatives and/or combinations thereof, preferably EGF and bFGF in combination;

(f) LIF

Standard culture media typically contains a variety of essential components required for cell viability, including inorganic salts, carbohydrates, hormones, essential amino acids, vitamins, and the like. We prefer DMEM or F-12 as the standard culture medium, most preferably a 50/50 mixture of DMEM and F-12. Both media are commercially available (DMEM—Gibco 12100-046; F-12 - Gibco 21700-075). A premixed formulation is also commercially available (N2 - Gibco 17502-030). It is advantageous to provide additional glutamine, preferably at about 2 mM. It is also advantageous to provide heparin in the culture medium. Preferably, the conditions for culturing should be as close to physiological as possible. The pH of the culture medium is typically between 6–8, preferably about 7, most preferably about 7.4. Cells are typically cultured between 30–40° C., preferably between 32–38° C., most preferably between 35–37° C. Cells are preferably grown in 5% $CO_2$. Cells are preferably grown in suspension culture.

In one exemplary embodiment, the neural stem cell culture comprises the following components in the indicated concentrations:

| Component | Final Concentration |
| --- | --- |
| 50/50 mix of DMEM/F-12 | 0.5–2.0 X, preferably 1X |
| glucose | 0.2–1.0%, preferably 0.6% w/v |
| glutamine | 0.1–10 mM, preferably 2 mM |
| NaHCO$_3$ | 0.1–10 mM, preferably 3 mM |
| HEPES | 0.1–10 mM, preferably 5 mM |
| apo-human transferrin (Sigma T-2252) | 1–1000 µg/ml, preferably 100 µg/ml |
| human insulin (Sigma I-2767) | 1–100, preferably 25 µg/ml |
| putrescine (Sigma P-7505) | 1–500, preferably 60 µM |

-continued

| Component | Final Concentration |
| --- | --- |
| selenium (Sigma S-9133) | 1–100, preferably 30 nM |
| progesterone (Sigma P-6149) | 1–100, preferably 20 nM |
| human EGF (Gibco 13247-010) | 0.2–200, preferably 20 ng/ml |
| human bFGF (Gibco 13256-029) | 0.2–200, preferably 20 ng/ml |
| human LIF (R&D Systems 250-L) | 0.1–500, preferably 10 ng/ml |
| heparin (Sigma H-3149) | 0.1–50, preferably 2 µg/ml |
| CO$_2$ | preferably 5% |

Serum albumin may also be present in the instant culture medium—although the present medium is generally serum-depleted or serum-free (preferably serum-free), certain serum components which are chemically well defined and highly purified (>95%), such as serum albumin, may be included.

The human neural stem cells described herein may be cryopreserved according to routine procedures. We prefer cryopreserving about one to ten million cells in "freeze" medium which consists of proliferation medium (absent the growth factor mitogens), 10% BSA (Sigma A3059) and 7.5% DMSO. Cells are centrifuged. Growth medium is aspirated and replaced with freeze medium. Cells are resuspended gently as spheres, not as dissociated cells. Cells are slowly frozen, by, e.g., placing in a container at −80° C. Cells are thawed by swirling in a 37° C. bath, resuspended in fresh proliferation medium, and grown as usual.

In another embodiment, this invention provides a differentiated cell culture containing previously unobtainable large numbers of neurons, as well as astrocytes and oligodendrocytes. In the prior art, typically the differentiated human diencephalon-derived neural stem cell cultures formed very few neurons (i.e., less than 5–10%). According to this methodology, we have routinely achieved neuron concentrations of between 20% and 35% (and much higher in other cases) in differentiated human forebrain-derived neural stem cell cultures. This is highly advantageous as it permits enrichment of the neuronal population prior to implantation in the host in disease indications where neuronal function has been impaired or lost.

Further, according to the methods of this invention, we have achieved differentiated neural stem cell cultures that are highly enriched in GABA-ergic neurons. Such GABA-ergic neuron enriched cell cultures are particularly advantageous in the potential therapy of excitotoxic neurodegenerative disorders, such as Huntington's disease or epilepsy.

In order to identify the cellular phenotype either during proliferation or differentiation of the neural stem cells, various cell surface or intracellular markers may be used.

When the neural stem cells of this invention are proliferating as neurospheres, we contemplate using human nestin antibody as a marker to identify undifferentiated cells. The proliferating cells should show little GFAP staining and little b-tubulin staining (although some staining might be present due to diversity of cells within the spheres).

When differentiated, most of the cells lose their nestin positive immunoreactivity. In particular, antibodies specific for various neuronal or glial proteins may be employed to identify the phenotypic properties of the differentiated cells. Neurons may be identified using antibodies to neuron specific enolase ("NSE"), neurofilament, tau, b-tubulin, or other known neuronal markers. Astrocytes may be identified using antibodies to glial fibrillary acidic protein ("GFAP"), or other known astrocytic markers. Oligodendrocytes may be identified using antibodies to galactocerebroside, O4, myelin basic protein ("MBP") or other known oligodendrocytic markers.

It is also possible to identify cell phenotypes by identifying compounds characteristically produced by those phenotypes. For example, it is possible to identify neurons by the production of neurotransmitters such as acetylcholine, dopamine, epinephrine, norepinephrine, and the like.

Specific neuronal phenotypes can be identified according to the specific products produced by those neurons. For example, GABA-ergic neurons may be identified by their production of glutamic acid decarboxylase ("GAD") or GABA. Dopaminergic neurons may be identified by their production of dopa decarboxylase ("DDC"), dopamine or tyrosine hydroxylase ("TH"). Cholinergic neurons may be identified by their production of choline acetyltransferase ("ChAT"). Hippocampal neurons may be identified by staining with NeuN. It will be appreciated that any suitable known marker for identifying specific neuronal phenotypes may be used.

The human neural stem cells described herein can be genetically engineered or modified according to known methodology.

A gene of interest (i.e., a gene that encodes a biologically active molecule) can be inserted into a cloning site of a suitable expression vector by using standard techniques. These techniques are well known to those skilled in the art. See, e.g., WO 94/16718, incorporated herein by reference.

The expression vector containing the gene of interest may then be used to transfect the desired cell line. Standard transfection techniques such as calcium phosphate co-precipitation, DEAE-dextran transfection, electroporation, biolistics, or viral transfection may be utilized. Commercially available mammalian transfection kits may be purchased from e.g., Stratagene. Human adenoviral transfection may be accomplished as described in Berg et al. *Exp. Cell Res.,* 192, pp. (1991). Similarly, lipofectamine-based transfection may be accomplished as described in Cattaneo, *Mol. Brain Res.,* 42, pp. 161–66 (1996).

A wide variety of host/expression vector combinations may be used to express a gene encoding a biologically active molecule of interest. See, e.g., U.S. Pat. No. 5,545,723, herein incorporated by reference, for suitable cell-based production expression vectors.

Increased expression of the biologically active molecule can be achieved by increasing or amplifying the transgene copy number using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841), all herein incorporated by reference.

The neural stem cells described herein, and their differentiated progeny may be immortalized or conditionally immortalized using known techniques. We prefer conditional immortalization of stem cells, and most preferably conditional immortalization of their differentiated progeny. Among the conditional immortalization techniques contemplated are Tet-conditional immortalization (see WO 96/31242, incorporated herein by reference), and Mx-1 conditional immortalization (see WO 96/02646, incorporated herein by reference).

This invention also provides methods for differentiating neural stem cells to yield cell cultures enriched with neurons to a degree previously unobtainable. According to one protocol, the proliferating neurospheres are induced to differentiate by removal of the growth factor mitogens and LIF, and provision of 1% serum, a substrate and a source of ionic charges (e.g., glass cover slip covered with poly-ornithine or extracellular matrix components). The preferred base medium for this differentiation protocol, excepting the growth factor mitogens and LIF, is otherwise the same as the proliferation medium. This differentiation protocol produces a cell culture enriched in neurons. According to this protocol, we have routinely achieved neuron concentrations of between 20% and 35% in differentiated human forebrain-derived neural stem cell cultures.

According to a second protocol, the proliferating neurospheres are induced to differentiate by removal of the growth factor mitogens, and provision of 1% serum, a substrate and a source of ionic charges (e.g., glass cover slip covered with poly-ornithine or extracellular matrix components), as well as a mixture of growth factors including PDGF, CNTF, IGF-1, LIF, forskolin, T-3 and NT-3. The cocktail of growth factors may be added at the same time as the neurospheres are removed from the proliferation medium, or may be added to the proliferation medium and the cells pre-incubated with the mixture prior to removal from the mitogens. This protocol produces a cell culture highly enriched in neurons and enriched in oligodendrocytes. According to this protocol, we have routinely achieved neuron concentrations of higher than 35% in differentiated human forebrain-derived neural stem cell cultures.

The human stem cells of this invention have numerous uses, including for drug screening, diagnostics, genomics and transplantation.

The cells of this invention may be transplanted "naked" into patients according to conventional techniques, into the CNS, as described for example, in U.S. Pat. Nos. 5,082,670 and 5,618,531, each incorporated herein by reference, or into any other suitable site in the body.

In one embodiment, the human stem cells are transplanted directly into the CNS. Parenchymal and intrathecal sites are contemplated. It will be appreciated that the exact location in the CNS will vary according to the disease state. According to one aspect of this invention, provided herein is methodology for improving the viability of transplanted human neural stem cells. In particular, we have discovered that graft viability improves if the transplanted neural stem cells are allowed to aggregate, or to form neurospheres prior to implantation, as compared to transplantation of dissociated single cell suspensions. We prefer transplanting small sized neurospheres, approximately 10–500 $\mu$m in diameter, preferably 40–50 $\mu$m in diameter. Alternatively, we prefer spheres containing about 5–100, preferably 5–20 cells per sphere. We contemplate transplanting at a density of about 10,000–1,000,000 cells per $\mu$l, preferably 25,000–500,000 cells per $\mu$l.

The cells may also be encapsulated and used to deliver biologically active molecules, according to known encapsulation technologies, including microencapsulation (see, e.g., U.S. Pat. Nos. 4,352,883; 4,353,888; and 5,084,350, herein incorporated by reference), (b) macroencapsulation (see, e.g., U.S. Pat. Nos. 5,284,761, 5,158,881, 4,976,859 and 4,968,733 and published PCT patent applications W092/19195, WO 95/05452, each incorporated herein by reference).

If the human neural stem cells are encapsulated, we prefer macroencapsulation, as described in U.S. Pat. Nos. 5,284,761; 5,158,881; 4,976,859; 4,968,733; 5,800,828 and published PCT patent application WO 95/05452, each incorporated herein by reference. Cell number in the devices can be varied; preferably each device contains between $10^3$–$10^9$ cells, most preferably $10^5$ to $10^7$ cells. A large number of macroencapsulation devices may be implanted in the patient; we prefer between one to 10 devices.

In addition, we also contemplate "naked" transplantation of human stem cells in combination with a capsular device wherein the capsular device secretes a biologically active molecule that is therapeutically effective in the patient or that produces a biologically active molecule that has a growth or trophic effect on the transplanted neural stem cells, or that induces differentiation of the neural stem cells towards a particular phenotypic lineage.

The cells and methods of this invention may be useful in the treatment of various neurodegenerative diseases and other disorders. It is contemplated that the cells will replace diseased, damaged or lost tissue in the host. Alternatively, the transplanted tissue may augment the function of the endogenous affected host tissue. The transplanted neural stem cells may also be genetically modified to provide a biologically active molecule that is therapeutically effective.

Excitotoxicity has been implicated in a variety of pathological conditions including epilepsy, stroke, ischemia, and neurodegenerative diseases such as Huntington's disease, Parkinson's disease and Alzheimer's disease. Accordingly, neural stem cells may provide one means of preventing or replacing the cell loss and associated behavioral abnormalities of these disorders.

Huntington's disease (HD) is an autosomal dominant neurodegenerative disease characterized by a relentlessly progressive movement disorder with devastating psychiatric and cognitive deterioration. HD is associated with a consistent and severe atrophy of the neostriatum which is related to a marked loss of the GABAergic medium-sized spiny projection neurons, the major output neurons of the striatum. Intrastriatal injections of excitotoxins such as quinolinic acid (QA) mimic the pattern of selective neuronal vulnerability seen in HD. QA lesions result in motor and cognitive deficits which are among the major symptoms seen in HD. Thus, intrastriatal injections of QA have become a useful model of HD and can serve to evaluate novel therapeutic strategies aimed at preventing, attenuating, or reversing neuroanatomical and behavioral changes associated with HD. Because GABA-ergic neurons are characteristically lost in Huntington's disease, we contemplate treatment of Huntington's patients by transplantation of cell cultures enriched in GABA-ergic neurons derived according to the methods of this invention.

Epilepsy is also associated with excitotoxicity. Accordingly, GABA-ergic neurons derived according to this invention are contemplated for transplantation into patients suffering from epilepsy.

We also contemplate use of the cells of this invention in the treatment of various demyelinating and dysmyelinating disorders, such as Pelizaeus-Merzbacher disease, multiple sclerosis, various leukodystrophies, post-traumatic demyelination, and cerebrovascular (CVS) accidents, as well as various neuritis and neuropathies, particularly of the eye. We contemplate using cell cultures enriched in oligodendrocytes or oligodendrocyte precursor or progenitors, such cultures prepared and transplanted according to this invention to promote remyelination of demyelinated areas in the host.

We also contemplate use of the cells of this invention in the treatment of various acute and chronic pains, as well as for certain nerve regeneration applications (such as spinal cord injury). We also contemplate use of human stem cells for use in sparing or sprouting of photoreceptors in the eye.

The cells and methods of this invention are intended for use in a mammalian host, recipient, patient, subject or individual, preferably a primate, most preferably a human.

The following examples are provided for illustrative purposes only, and are not intended to be limiting.

EXAMPLES

Example 1

Media for Proliferating Neural Stem Cells

Proliferation medium was prepared with the following components in the indicated concentrations:

| Component | Final Concentration |
| --- | --- |
| 50/50 mix of DMEM/F-12 | 1X |
| glucose | 0.6% w/v |
| glutamine | 2 mM |
| NaHCO$_3$ | 3 mM |
| HEPES | 5 mM |
| apo-human transferrin (Sigma T-2252) | 100 µg/ml |
| human insulin (Sigma I-2767) | 25 µg/ml |
| putrescine (Sigma P-7505) | 60 µM |
| selenium (Sigma S-9133) | 30 nM |
| progesterone (Sigma P-6149) | 20 nM |
| human EGF (Gibco 13247-010) | 20 ng/ml |
| human bFGF (Gibco 13256-029) | 20 ng/ml |
| human LIF (R&D Systems 250-L) | 10 ng/ml |
| heparin (Sigma H-3149) | 2 µg/ml |

Example 2

Isolation of Human CNS Neural Stem Cells

Sample tissue from human embryonic forebrain was collected and dissected in Sweden and kindly provided by Huddinje Sjukhus. Blood samples from the donors were sent for viral testing. Dissections were performed in saline and the selected tissue was placed directly into proliferation medium (as described in Example 1). Tissue was stored at 4° C. until dissociated. The tissue was dissociated using a standard glass homogenizer, without the presence of any digesting enzymes. The dissociated cells were counted and seeded into flasks containing proliferation medium. After 5–7 days, the contents of the flasks are centrifuged at 1000 rpm for 2 min. The supernatant was aspirated and the pellet resuspended in 200 µl of proliferation medium. The cell clusters were triturated using a P200 pipetman about 100 times to break up the clusters. Cells were reseeded at 75,000–100,000 cells/ml into proliferation medium. Cells were passaged every 6–21 days depending upon the mitogens used and the seeding density. Typically these cells incorporate BrdU, indicative of cell proliferation. For T75 flask cultures (initial volume 20 ml), cells are "fed" 3 times weekly by addition of 5 ml of proliferation medium. We prefer Nunc flasks for culturing.

Nestin Staining for Proliferating Neurospheres

We stained for nestin (a measure of proliferating neurospheres) as follows. Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1 M PBS, pH 7.4 and 1% Triton X-100 (Sigma X-100) for 1 hr at room temperature with gentle shaking. Cells were incubated with primary antibodies to human nestin (from Dr. Lars Wahlberg, Karolinska, Sweden, rabbit polyclonal used at 1:500) diluted in 1% NGS and 1% Triton X-100 for 2 hr at room temperature. Preparations were then washed twice for 5 min with 0.1 M PBS. Cells were incubated with secondary antibodies (pool of GAM/FITC used at 1:128, Sigma F-0257; GAR/TRITC used at 1:80, Sigma T-5268) diluted in 1% NGS and 1% Triton X-100 for 30 min at room temperature in the dark. Preparations are washed twice for 5 min with 0.1 M PBS in the dark. Preparations are mounted onto slides face down with mounting medium (Vectashield Mounting Medium, Vector Labs., H-1000) and stored at 4° C.

FIG. 1 shows a picture of proliferating spheres (here called "neurospheres") of human forebrain derived neural stem cells. We evaluated proliferation of 4 lines of human forebrain derived neural stem cells in proliferation medium as described above with LIF present of absent.

As FIG. 2 shows, in three of the four lines (6.5 Fbr, 9 Fbr, and 10.5 FBr), LIF significantly increased the rate of cell proliferation. The effect of LIF was most pronounced after about 60 days in vitro.

Figure 3:
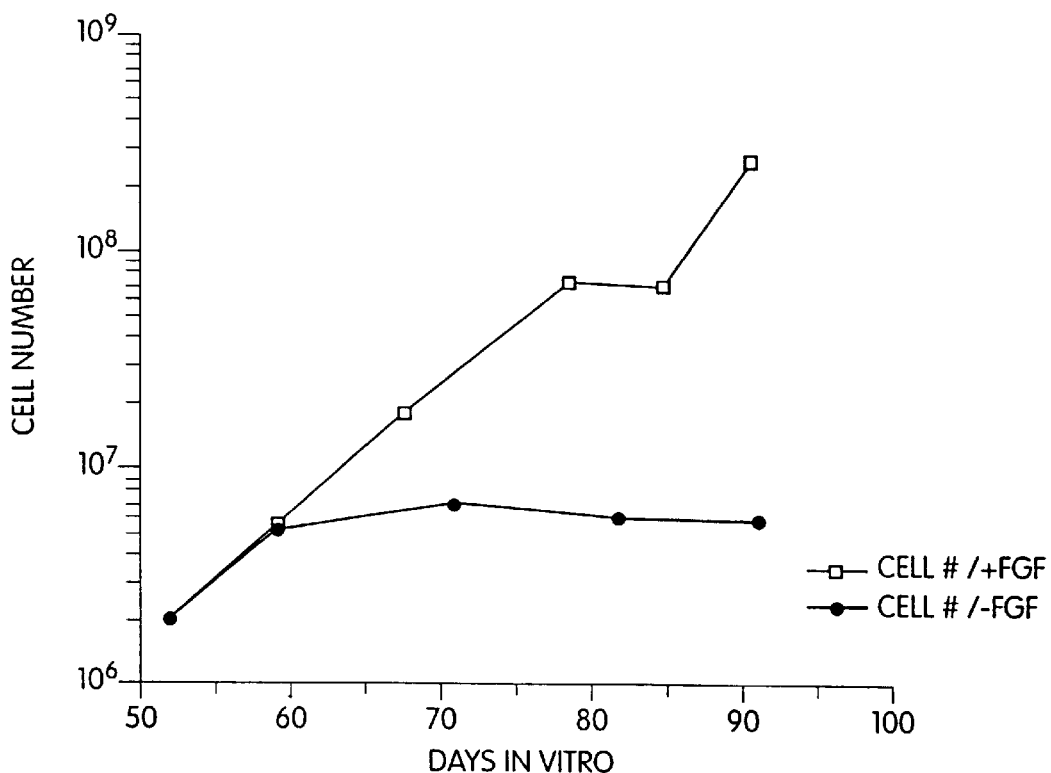
FIG. 3 shows a growth curve for a human neural stem cell line designated 9 Fbr cultured in (a) defined media containing EGF and basic fibroblast growth factor ("bFGF") (shown as open diamonds), and (b) defined media with EGF but without bFGF (shown as closed diamonds).

We also evaluated the effect of bFGF on the rate of proliferation of human forebrain-derived neural stem cells. As FIG. 3 shows, in the presence of bFGF, the stem cells proliferation was significantly enhanced.

Example 3

Differentiation of Human Neural Stem Cells

In a first differentiation protocol, the proliferating neurospheres were induced to differentiate by removal of the growth factor mitogens and LIF, and provision of 1% serum, a substrate and a source of ionic charges(e.g., glass cover slip covered with poly-ornithine).

The staining protocol for neurons, astrocytes and oligodendrocytes was as follows:

β-Tubulin Staining for Neurons

Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1 M PBS, pH 7.4. Cells were incubated with primary antibodies to b-tubulin (Sigma T-8660, mouse monoclonal; used at 1: 1,000) diluted in 1% NGS for 2 hr at room temperature. Preparations were then washed twice for 5 min with 0.1 M PBS. Cells were incubated with secondary antibodies (pool of GAM/FITC used at 1:128, Sigma F-0257; GAR/TRITC used at 1:80, Sigma T-5268) diluted in 1% NGS for 30 min at room temperature in the dark. Preparations are washed twice for 5 min with 0.1 M PBS in the dark. Preparations are mounted onto slides face down with mounting medium (Vectashield Mounting Medium, Vector Labs., H1000) and stored at 4° C.

In some instances we also stain with DAPI (a nuclear stain), as follows. Coverslips prepared as above are washed with DAPI solution (diluted 1:1000 in 100% MeOH, Boehringer Mannheim, # 236 276). Coverslips are incubated in DAPI solution for 15 min at 37° C.

O4 Staining for Oligodendrocvtes

Cells were fixed for 10 min at room temperature with 4% paraformaldehyde. Cells were washed three times for 5 min with 0.1 M PBS, pH 7.4. Cell preparations were blocked for 1 hr at room temperature in 5% normal goat serum ("NGS") diluted in 0.1 M PBS, pH 7.4. Cells were incubated with primary antibodies to O4 (Boehringer Mannheim # 1518 925, mouse monoclonal; used at 1:25) diluted in 1% NGS for 2 hr at room temperature. Preparations were then washed twice for 5 min with 0.1 M PBS. Cells were incubated with secondary antibodies, and further processed as described above for b-tubulin.

GFAP Staining for Astrocytes

Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1 M PBS, pH 7.4. Cells were incubated with primary antibodies to GFAP (DAKO Z 334, rabbit polyclonal; used at 1:500) diluted in 1% NGS for 2 hr at room temperature. Preparations were then washed twice for 5 min with 0.1 M PBS. Cells were incubated with secondary antibodies, and further processed as described above for b-tubulin.

This differentiation protocol produced cell cultures enriched in neurons as follows:

| Cell Line | Passage | % GFAP Positive | % b-tubulin positive | % of neurons that are GABA positive |
|---|---|---|---|---|
| 6.5 FBr | 5 | 15 | 37 | 20 |
| 9 FBr | 7 | 52 | 20 | 35 |
| 10.5 FBr | 5 | 50 | 28 | 50 |

We also evaluated the ability of a single cell line to differentiate consistently as the culture aged (i.e., at different passages), using the above differentiation protocol. The data are as follows:

| Cell Line | Passage | % GFAP Positive | % b-tubulin positive | % of neurons that are GABA positive |
|---|---|---|---|---|
| 9 FBr | 7 | 53 | 20.4 | ND |
| 9 FBr | 9 | ND | 20.3 | 34.5 |
| 9 FBr | 15 | 62 | 17.9 | 37.9 |

We conclude from these data that cells will follow reproducible differentiation patterns irrespective of passage number or culture age.

Example 4

Differentiation of Human Neural Stem Cells

In a second differentiation protocol, the proliferating neurospheres were induced to differentiate by removal of the growth factor mitogens and LIF, and provision of 1% serum, a substrate (e.g., glass cover slip or extracellular matrix components), a source of ionic charges (e.g., poly-ornithine) as well as a mixture of growth factors including 10 ng/ml PDGF A/B, 10 ng/ml CNTF, 10 ng/ml IGF-1, 10 $\mu$M forskolin, 30 ng/ml T3, 10 ng/ml LIF and 1 ng/ml NT-3. This differentiation protocol produced cell cultures highly enriched in neurons (i.e., greater than 35% of the differentiated cell culture) and enriched in oligodendrocytes.

Example 5

Genetic Modification

We have conditionally immortalized a glioblast cell line derived from the human neural stem cells described herein, using the Mx-1 system described in WO 96/02646. In the Mx-1 system, the Mx-1 promoter drives expression of the SV40 large T antigen. The Mx-1 promoter is induced by interferon. When induced, large T is expressed, and quiescent cells proliferate.

Figure 4:
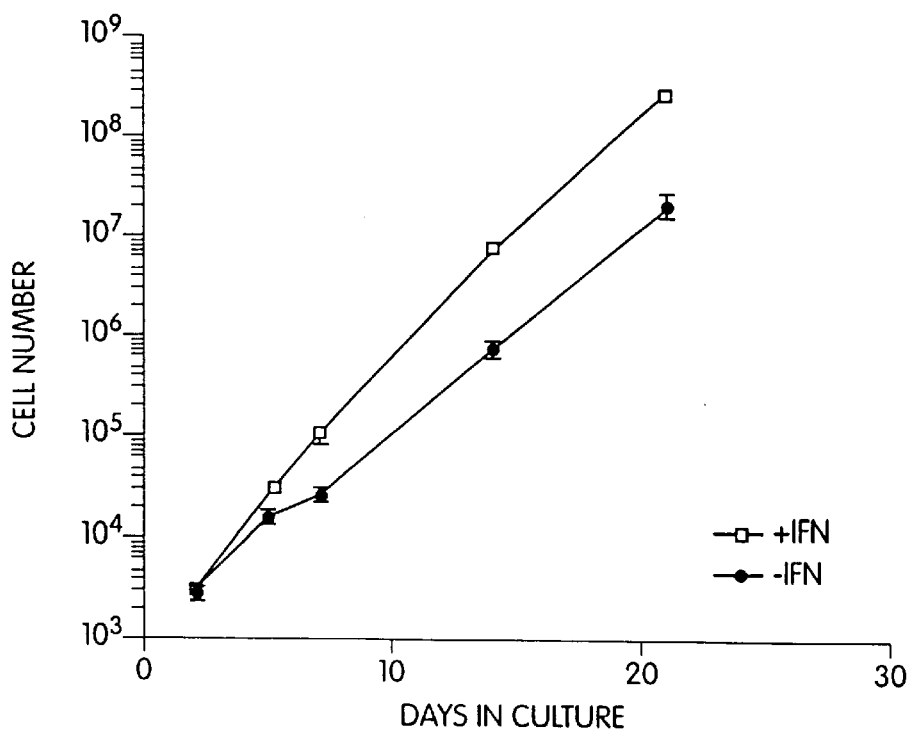
FIG. 4 shows a graph of cell number versus days in culture for an Mx-1 conditionally immortalized human glioblast line derived from a human neural stem cell line. The open squares denote growth in the presence of interferon, the closed diamonds denote growth in the absence of interferon.

Human glioblasts were derived from human forebrain neural stem cells as follows. Proliferating human neurospheres were removed from proliferation medium and plated onto poly-ornithine plastic (24 well plate) in a mixture of N2 with the mitogens EGF, bFGF and LIF, as well as 0.5% FBS. 0.5 ml of N2 medium and 1% FBS was added. The cells were incubated overnight. The cells were then transfected with p318 (a plasmid containing the Mx-1 promoter operably linked to the SV 40 large T antigen) using Invitrogen lipid kit (lipids 4 and 6). The transfection solution contained 6 µl/ml of lipid and 4 µl/ml DNA in optiMEM medium. The cells were incubated in transfection solution for 5 hours. The transfection solution was removed and cells placed into N2 and 1% FBS and 500 U/ml A/D interferon. The cells were fed twice a week. After ten weeks cells were assayed for large T antigen expression. The cells showed robust T antigen staining at this time. As FIG. 4 shows, cell number was higher in the presence of interferon than in the absence of interferon.

Large T expression was monitored using immunocytochemistry as follows. Cells were fixed for 20 min at room temperature with 4% paraformaldehyde. Cells were washed twice for 5 min with 0.1 M PBS, pH 7.4. Cells were permeabilized for 2 min with 100% EtOH. The cells were then washed twice for 5 min with 0.1 M PBS. Cell preparations were blocked for 1 hr at room temperature in 5% normal goat serum ("NGS") diluted in 0.1 M PBS, pH 7.4. Cells were incubated with primary antibodies to large T antigen (used at 1:10) diluted in 1% NGS for 2 hr at room temperature. We prepared antibody to large T antigen in house by culturing PAB 149 cells and obtaining the conditioned medium. Preparations were then washed twice for 5 min with 0.1 M PBS. Cells were incubated with secondary antibodies (goat-anti-mouse biotinylated at 1:500 from Vector Laboratories, Vectastain Elite ABC mouse IgG kit, PK-6102) diluted in 1% NGS for 30 min at room temperature. Preparations are washed twice for 5 min with 0.1 M PBS. Preparations are incubated in ABC reagent diluted 1:500 in 0.1 M PBS, pH 7.4 for 30 min at room temperature. Cells are washed twice for 5 min in 0.1 M PBS, pH 7.4, then washed twice for 5 min in 0.1 M Tris, pH 7.6. Cells are incubated in DAB (nickel intensification) for 5 min at room temperature. The DAB solution is removed, and cells are washed three to five times with dH20. Cells are stored in 50% glycerol/50% 0.1 M PBS, pH 7.4.

Example 6

Encapsulation

If the human neural stem cells are encapsulated, then the following procedure may be used:

The hollow fibers are fabricated from a polyether sulfone (PES) with an outside diameter of 720 m and a wall thickness of a 100 m (AKZO-Nobel Wüppertal, Germany). These fibers are described in U.S. Pat. Nos. 4,976,859 and 4,968,733, herein incorporated by reference. The fiber may be chosen for its molecular weight cutoff. We sometimes use a PES#5 membrane which has a MWCO of about 280 kd. In other studies we use a PES#8 membrane which has a MWCO of about 90 kd.

The devices typically comprise:

1) a semipermeable poly (ether sulfone) hollow fiber membrane fabricated by AKZO Nobel Faser AG;
2) a hub membrane segment;
3) a light cured methacrylate (LCM) resin leading end; and
4) a silicone tether.

The semipermeable membrane used typically has the following characteristics:

| | |
|---|---|
| Internal Diameter | 500 + 30 m |
| Wall Thickness | 100 + 15 m |
| Force at Break | 100 + 15 cN |
| Elongation at Break | 44 + 10% |
| Hydraulic Permeability | 63 + 8 (ml/min m$^2$ mmHg) |
| nMWCO (dextrans) | 280 + 20 kd |

The components of the device are commercially available. The LCM glue is available from Ablestik Laboratories (Newark, Del.); Luxtrak Adhesives LCM23 and LCM24). The tether material is available from Specialty Silicone Fabricators (Robles, Calif.). The tether dimensions are 0.79 mm OD×0.43 mm ID×length 202 mm. The morphology of the device is as follows: The inner surface has a permselective skin. The wall has an open cell foam structure. The outer surface has an open structure, with pores up to 1.5 m occupying 30+5% of the outer surface.

Fiber material is first cut into 5 cm long segments and the distal extremity of each segment sealed with a photopolymerized acrylic glue (LCM-25, ICI). Following sterilization with ethylene oxide and outgassing, the fiber segments are loaded with a suspension of between $10^4$–$10^7$ cells, either in a liquid medium, or a hydrogel matrix (e.g., a collagen solution (Zyderm®), alginate, agarose or chitosan) via a Hamilton syringe and a 25 gauge needle through an attached injection port. The proximal end of the capsule is sealed with the same acrylic glue. The volume of the device contemplated in the human studies is approximately 15–18 1.

A silicone tether (Specialty Silicone Fabrication, Taunton, Mass.) (ID: 690 m; OD: 1.25 mm) is placed over the proximal end of the fiber allowing easy manipulation and retrieval of the device.

Example 8

Transplantation of Neural Stem Cells

We have transplanted human neural stem cells into rat brain and assessed graft viability, integration, phenotypic fate of the grafted cells, as well as behavioral changes associated with the grafted cells in lesioned animals.

Transplantation was performed according to standard techniques. Adult rats were anesthetized with sodium pentobarbitol (45 mg/kg, i.p.) And positioned in a Kopf stereotaxic instrument. A midline incision was made in the scalp and a hole drilled for the injection of cells. Rats received implants of unmodified, undifferentiated human neural stem cells into the left striatum using a glass capillary attached to a 10 µl Hamilton syringe. Each animal received a total of about 250,000–500,000 cells in a total volume of 2 µl. Cells were transplanted 1–2 days after passaging and the cell suspension was made up of undifferentiated stem cell clusters of 5–20 cells. Following implantation, the skin was sutured closed.

Animals were behaviorally tested and then sacrificed for histological analysis.

I claim:

1. A culture medium for proliferating mammalian neural stem cells, the media comprising cell viability and cell proliferation effective amounts of the following components:

(a) a standard defined basal medium;

(b) a supplemental carbohydrate, wherein the carbohydrate is present at a concentration between 0.2% and 1.0% weight/volume (w/v);

(c) a supplemental buffer, such that the pH of the culture medium is between pH 6 and pH 8;

(d) supplemental agents, wherein the agents are selected from the group consisting of insulin, transferrin, progesterone, selenium, putrescine, and combinations thereof;

(e) one or more growth factors that stimulate proliferation of neural stem cells, wherein the growth factors are present at a concentration of between 0.2 ng/ml and 200 ng/ml, and;

(f) leukocyte inhibitory factor (LIF), wherein the LIF is present at a concentration of between 0.1 ng/ml and 500 ng/ml.

2. The medium of claim 1 further comprising heparin.

* * * * *

UNITED STATES PATENT AND TRADEMARK OFFICE
CERTIFICATE OF CORRECTION

PATENT NO. : 6,103,530
DATED : August 15, 2000
INVENTOR(S) : Melissa Carpenter

It is certified that error appears in the above-identified patent and that said Letters Patent is hereby corrected as shown below:

Column 14, line 5, "leukocyte inhibitory factor (LIF)" should read --leukemia inhibitory factor (LIF)--

Signed and Sealed this

Fifth Day of June, 2001

Attest:

*Attesting Officer*

NICHOLAS P. GODICI

*Acting Director of the United States Patent and Trademark Office*

(12) EX PARTE REEXAMINATION CERTIFICATE (6505th)
United States Patent
Carpenter

(10) Number: US 6,103,530 C1
(45) Certificate Issued: Nov. 4, 2008

(54) CULTURES OF HUMAN CNS NEURAL STEM CELLS

(75) Inventor: Melissa Carpenter, Lincoln, RI (US)

(73) Assignee: Stemcells California, Inc., Palo Alto, CA (US)

Reexamination Request:
No. 90/008,862, Oct. 2, 2007

Reexamination Certificate for:
Patent No.: 6,103,530
Issued: Aug. 15, 2000
Appl. No.: 09/178,035
Filed: Oct. 23, 1998

Certificate of Correction issued Jun. 5, 2001.

Related U.S. Application Data

(62) Division of application No. 08/926,313, filed on Sep. 5, 1997, now Pat. No. 5,968,829.

(51) Int. Cl.
*A61K 35/12* (2006.01)
*A61K 48/00* (2006.01)
*C12N 5/06* (2006.01)
*G01N 33/50* (2006.01)

(52) U.S. Cl. .................. 435/405; 435/325; 435/384; 435/389; 435/406; 435/404; 435/387; 435/377; 435/368

(58) Field of Classification Search .................. None
See application file for complete search history.

(56) References Cited

U.S. PATENT DOCUMENTS

| | | |
|---|---|---|
| 5,166,065 A | 11/1992 | Williams et al. |
| 5,851,832 A | 12/1998 | Weiss et al. |
| 6,497,872 B1 | 12/2002 | Weiss et al. |

OTHER PUBLICATIONS

Amendment Under 37 C.F.R. 1.111 for U.S. Appl. No. 09/178,035, filed May 21, 1999.

"Leukaemia Inhibitory Factor is Necessary for Maintenance of Haematopoietic Stem Cells and Thymocyte Stimulation" written by Jean–Louis Escary, et al., vol. 363, published May 27, 1993, pp. 361–364.

"Long–term Proliferation of Mouse Primordial Germ Cells in Culture" written by James L. Resnick, et al., vol. 359, published Oct. 8, 1992, pp. 550–551.

"Ciliary Neuroptrophic Factor Maintains the Pluripotentiality of Embryonic Stem Cells" written by Joanne C. Conover, et al., published in 1993, pp. 559–565.

*Primary Examiner*—Bennett Celsa

(57) ABSTRACT

Isolation, characterization, proliferation, differentiation and transplantation of mammalian neural stem cells is disclosed.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claim 2, dependent on an amended claim, is determined to be patentable.

1. A culture medium for proliferating [mammalian] *human* neural stem cells, the media comprising cell viability and cell proliferation effective amounts of the following components:

(a) a standard defined basal medium *that is serum-free*;

(b) a supplemental carbohydrate, wherein the carbohydrate is present at a concentration between 0.2% and 1.0% weight/volume (w/v);

(c) a supplemental buffer, such that the pH of the culture medium is between pH 6 and pH 8;

(d) supplemental agents, wherein the agents are selected from the group consisting of insulin, transferrin, progesterone, selenium, putrescine, and combinations thereof;

(e) [one or more] *a combination of* growth factors that stimulate proliferation of *human* neural stem cells, wherein the growth factors are present at a concentration of between 0.2 ng/ml and 200 ng/ml, and *wherein the growth factors are human EGF and human bFGF*;

*human* leukemia inhibitory factor (LIF), wherein the LIF is present at a concentration of between 0.1 ng/ml and 500 ng/ml.

* * * * *